United States Patent
Simpson et al.

(10) Patent No.: US 9,611,304 B2
(45) Date of Patent: Apr. 4, 2017

(54) TNNT1 MINI-PROMOTERS

(71) Applicant: The University of British Columbia, Vancouver (CA)

(72) Inventors: Elizabeth M. Simpson, Vancouver (CA); Vikramjit Chopra, Vancouver (CA); Cletus D'Souza, Vancouver (CA); Charles de Leeuw, Seattle, WA (US); Daniel Goldowitz, Port Moody (CA); Robert A. Holt, North Vancouver (CA); Steven J. Jones, Vancouver (CA); Elodie Portales-Casamar, Vancouver (CA); Wyeth W. Wasserman, Vancouver (CA)

(73) Assignee: The University of British Columbia, British Columbia (CA)

( * ) Notice: Subject to any disclaimer, the term of this patent is extended or adjusted under 35 U.S.C. 154(b) by 0 days.

(21) Appl. No.: 14/724,544

(22) Filed: May 28, 2015

(65) Prior Publication Data

US 2015/0343020 A1    Dec. 3, 2015

Related U.S. Application Data

(60) Provisional application No. 62/004,807, filed on May 29, 2014.

(51) Int. Cl.
| | |
|---|---|
| *A61K 38/17* | (2006.01) |
| *C07K 14/47* | (2006.01) |
| *C12N 15/86* | (2006.01) |
| *A61K 48/00* | (2006.01) |
| *A61K 38/00* | (2006.01) |

(52) U.S. Cl.
CPC .......... *C07K 14/47* (2013.01); *C07K 14/4716* (2013.01); *C12N 15/86* (2013.01); *A61K 38/00* (2013.01); *A61K 48/00* (2013.01)

(58) Field of Classification Search
None
See application file for complete search history.

(56) References Cited

U.S. PATENT DOCUMENTS

2004/0110221 A1*  6/2004  Twine .................. C12Q 1/6886
                                                   435/6.11

OTHER PUBLICATIONS

Kuwayama; Cell Interaction; Chapter 9, Enhancement of Homologous Recombination Efficiency by Homologous Oligonucleotides; published Oct. 10, 2012, pp. 233-244.*
Johnston et al., "A novel nemaline myopathy in the Amish caused by a mutation in troponin T1", Am J Hum Genet Aug. 21, 2000, pp. 814-821, 67, The American Society of Human Genetics, Bethesda, MD.
Kee et al., "Tropomyosins in skeletal muscle diseases", Adv Exp Med Biol, 2008, pp. 143-157, (644), Springer, Berlin, Germany.
Manuylov et al., "Cardiac expression of Tnnt1 requires the GATA4-FOG2 transcription complex", The Scientific World Journal, Jul. 4, 2009, pp. 575-587,(9), Hindawi Publishing Corporation, New York, NY.
Lowe et al., "The expression of Troponin T1 gene is induced by ketamine in adult mouse brain", Brain Res., Oct. 12, 2007, pp. 7-17, vol. 1174, Elsevier, Amsterdam, Netherlands.

* cited by examiner

*Primary Examiner* — Antonio Galisteo Gonzalez
(74) *Attorney, Agent, or Firm* — Pamela J. Sherwood; Bozicevic, Field & Francis LLP

(57) ABSTRACT

Isolated polynucleotides comprising a TNNT1 mini-promoters are provided. The mini-promoter may be operably linked to an expressible sequence, e.g. reporter genes, genes encoding a polypeptide of interest, regulatory RNA sequences such as miRNA, siRNA, anti-sense RNA, etc., and the like. In some embodiments a cell comprising a stable integrant of an expression vector is provided, which may be integrated in the genome of the cell. The promoter may also be provided in a vector, for example in combination with an expressible sequence. The polynucleotides find use in a method of expressing a sequence of interest, e.g. for identifying or labeling cells, monitoring or tracking the expression of cells, gene therapy, etc.

8 Claims, 3 Drawing Sheets
(3 of 3 Drawing Sheet(s) Filed in Color)

Ple232-lacZ (*TNNT1* RRs)

Ple301-icre in ssAAV9 virus vEMS48
Quadriceps @ P21
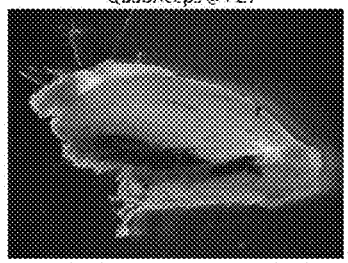
Heart @ P21
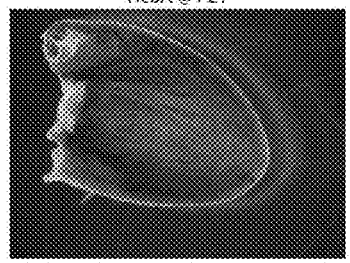
Quadriceps @ P56
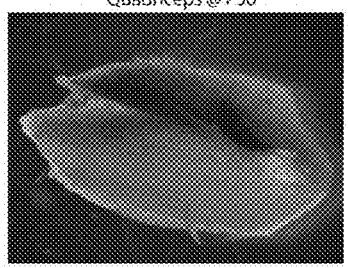
Heart @ P56
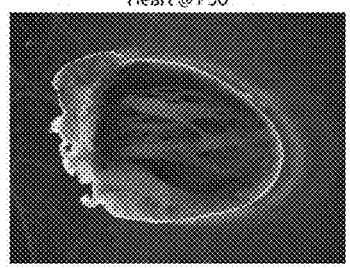
Figure 3A            Figure 3B

SEQUENCE LISTING

<160> NUMBER OF SEQ ID NOS: 9

<210> SEQ ID NO 1
<211> LENGTH: 1209
<212> TYPE: DNA
<213> ORGANISM: Homo sapiens

<400> SEQUENCE: 1
gaaaacttag agtgccatta tctggggtat catgaactgg gcctccgagt ttgggtatca      60
agattttggg ggtctcatat tcttgaggtt tcagatttta ggaggtctca agacctgggg     120
gtggtcttag gatgtcccgg cccatatctg gactatcaag aactgggatt tcagaatcca     180
gagctgtgag gacttgctgg cctcagaaac acgggcatca taaatcgggg tctcagaatc     240
tgtgggtatt gggatttggg gctaggcacc ctgtggccta gggtgtctca aagactttga     300
ggtctaagaa tgtaggggtc agggtgaggt ctacggacag aaggtgccct ttatgcccct     360
gccccctacg tgatgtatgg gaaggtgaaa ggggagacag gtgggagga aaccagccag     420 tggggtgggg cgagtgggag aggggatgcg ggtgactaat tctcccagaa gccccccttc     480
ctcaaatccc ttcttaggaa atgtcctcgg tttcaccatc tatgacatcc ccccaaaata     540
gctcctgggg gtggggcagc tattgtcttc aggccactgt cccttctcaa atgcctcttc     600
ctaatcccaa ctggatcagg ttcccatgga cttgtcataa gacaaaagag gacagctgtg     660 ctgaggggc agggtctgca gcctcctggc tgtgccagga ccacacctac caaggtctgt     720
cctcatgcat gctttaggac agccggcccc ctccctcaga cccaagagtc cagacctgag     780
ccctcctccc tcagacgcag gagtacaggc cccagcccg ctcctccctc agactcagga     840
gtctagactc ccagcctctc ccctccaagg acctactgtg tgccgggcat gggacgtca     900 aagcacaggg agctataagg gaggtagttg gagcaccacg ggagcctggg gtgtggggtg     960
ggagcagggg cggggctcct gggccatgca gatggggttg gcatgggtt ggggagggc    1020 ccacggaggc ttctggactc tgagtgtgga gccagggca gcaggctgt ctctgaactc    1080 ccaggcttgt gtttgagcaa aggaattctc tccccctccc tctcccctcg ggcgggccc    1140

```
gagcctccag ctataaactc cccggagctt cagtgccctc agcaaggctc agcctcaaga      1200
ttcacagca                                                              1209
```

<210> SEQ ID NO 2
<211> LENGTH: 1209
<212> TYPE: DNA
<213> ORGANISM: Homo sapiens

<400> SEQUENCE: 2

```
gaaaacttag agtgccatta tctggggtat catgaactgg gcctccgagt ttgggtatca       60
agattttggg ggtctcatat tcttgaggtt tcagattta ggaggtctca agacctgggg      120
gtggtcttag gatgtcccgg cccatatctg gactatcaag aactgggatt tcagaatcca      180
gagctgtgag gacttgctgg cctcagaaac acgggcatca taaatcgggg tctcagaatc      240
tgtgggtatt gggatttggg gctaggcacc ctgtggccta gggtgtctca aagactttga      300
ggtctaagaa tgtaggggtc agggtgaggt ctacggacag aaggtgccct ttatgcccct      360 gcccctacg tgatgtatgg aaggtgaaa ggggagacag gtgggagga aaccagccag         420 tggggtgggg cgagtgggag aggggatgcg ggtgactaat tctcccagaa gcccccttc       480 ctcaaatccc ttcttaggaa atgtcctcgg tttcaccatc tatgacatcc ccccaaaata      540
gctcctgggg gtggggcagc tattgtcttc aggccactgt cccttctcaa atgcctcttc      600
ctaatcccaa ctggatcagg ttcccatgga cttgtcataa gacaaaagag gacagctgtg      660
ctgagggggc agggtctgca gcctcctggc tgtgccagga ccacacctac caaggtctgt      720
cctcatgcat gctttaggac agccggcccc ctccctcaga cccaagagtc cagacctgag      780
ccctcctccc tcagacgcag gagtacaggc cccagcccg ctcctccctc agactcagga       840
gtctagactc ccagcctctc ccctccaagg acctactgtg tgccgggcat ggggacgtca      900
aagcacaggg agctataagg gaggtagttg gagcaccacg ggagcctggg gtgtggggtg      960
ggagcagggg cggggctcct gggccatgca gatgggttg gcatgggtt ggggagggc        1020 ccacggaggc ttctggactc tgagtgtgga gccaggggca gcagggctgt ctctgaactc     1080
ccaggcttgt gtttgagcaa aggaattctc tccccctccc tctcccctcg gggcgggccc     1140
gagcctccag ctataaactt cccggagctt ctgtgccctc agcaaggctc agcctcaaga     1200
ttcacagca                                                             1209
```

<210> SEQ ID NO 3
<211> LENGTH: 1258
<212> TYPE: DNA
<213> ORGANISM: Homo sapiens

<400> SEQUENCE: 3

```
aaataccaca agatgcatag aaggaagtgc aaagaaagga gaaagagag acagagatat        60 actcacagca aggtgcagag acatggagac cctataagag atggaaatgg agagccacag     120 aggggggaact gcgggcacta agagagacat ggagagaact agaaagatag agacgtgaac     180
acagacacag agacccagag ccaaaaagag acagaaatgg ggtcataggt ggacagaaat     240
gcacagagag actgtgagcc cccacagaca caaacgctga gaggggcaga catgcagaga     300
cacccacaga aatgcagaga caaaaccacc cggagacaca tgccgagaaa cacactgagg     360
ggctcagaaa gcgacagatg cagagagagc ccaagacaga cccagcaagg gccccgaga      420 aatgcacaga aacacaaaga ccgagaccac cagagacaga ggtacggaga ggcggggagg     480
gtgaggaagc ctgctctcca gggctggctt gaacctagaa ctcaaggtca tggcttggct     540
```

| | | |
|---|---|---|
| gggaagcggg aggggggatac caaaaaagat cagcgttaga tggaggtggg gagggagggt | 600 |
| aggtttcacc ctaattgaca ccccacccctc ccctcccc tccccacacc tgcttcccgg | 660 |
| ctttagtgcc tgttgtcacc aggatggaat cctggcggca gacaaagggg tgggggtggg | 720 |
| aggaggagac aaaaagatgg acagagacag aggaggagac taagaagtag agacagacac | 780 |
| acagagacac acagatggag agccacagag acaacagaaa tgggggtcca gaaagagacc | 840 |
| tagatagaaa gagggaacag agagaagaaa acaggaaaca ttccttatag cccatgtgtc | 900 |
| attagtaggt cctccaagga cctactgtgt gccgggcatg gggacgtcaa agcacaggga | 960 |
| gctataaggg aggtagttgg agcaccacgg gagcctgggg tgtggggtgg gagcagggc | 1020 |
| ggggctcctg ggccatgcag atggggttgg catgggttg ggaggggcc cacggaggct | 1080 |
| tctggactct gagtgtggag ccaggggcag cagggctgtc tctgaactcc caggcttgtg | 1140 |
| tttgagcaaa ggaattctct cccctccct ctccctcgg ggcgggcccg agcctccagc | 1200 |
| tataaactcc ccggagcttc agtgccctca gcaaggctca gcctcaagat tcacagca | 1258 |

<210> SEQ ID NO 4
<211> LENGTH: 1216
<212> TYPE: DNA
<213> ORGANISM: Homo sapiens

<400> SEQUENCE: 4

| | | |
|---|---|---|
| gtaaccgcgg ctgcttcgct tcccgagacc gatgtcgggg gcccgggggg accccgata | 60 |
| tcctcgggcc ccaacctcca agaccaccct tccctccctc cgccccata acccgccccc | 120 |
| aggcccggtc ctttaagccc ctgagagctc ctgcgccctc tcggggccgg aagggaaat | 180 |
| ggccccgcag tggctttaac cctttccctt ccttcttaaa gggaccgaca cccaagcctt | 240 |
| cttccccagt ctggaggaat cttttacagaa gggttggatg tttgcggaga agcaccaccc | 300 |
| catccccct tatcttcgcc tccaaccttg tctgttattt tctcccccat atacattcaa | 360 |
| aggttgggc ttggaattta ggattgcaga ggaggcgagc gctgggagtc agggtctcca | 420 |
| aggtcgggcc gggggcgggg gggcggtggg gcggtgggca ggggcgagc tggggagaga | 480 |
| gcgctggggt cactgaatga agacagaggt tgggaccccc tgcactgctg ggtcctaatg | 540 |
| gaggagagca ggagctctgg gcatataaat agagaaaggt ctgggggttt gcactcctgg | 600 |
| gtgtgcagac agtgggggtg gggggtcccc acaccagttc tgaatgtata tctgatgcgt | 660 |
| gtgaccctct tcctcctta cagccaccct gactttcctt ccctcttttc ttctccccat | 720 |
| cccccctcct ccagaactgg actccagagt ccttccctgg ggtcctgggg gccgaggctt | 780 |
| gggggggtccc tccccagggt gtgtcaggcc tagcccctct cctctaaact cttgctaatt | 840 |
| atctcttttt atccccacc accaacagcc tccaaggacc tactgtgtgc cgggcatggg | 900 |
| gacgtcaaag cacagggagc tataagggag gtagttggag caccacggga gcctggggtg | 960 |
| tggggtggga gcaggggcgg ggctcctggg ccatgcagat ggggttggca tgggttggg | 1020 |
| gaggggccca cggaggcttc tggactctga gtgtggagcc aggggcagca gggctgtctc | 1080 |
| tgaactccca ggcttgtgtt tgagcaaagg aattctctcc ccctccctct ccctcgggg | 1140 |
| cgggcccgag cctccagcta taaactcccc ggagcttcag tgccctcagc aaggctcagc | 1200 |
| ctcaagattc acagca | 1216 |

<210> SEQ ID NO 5
<211> LENGTH: 348
<212> TYPE: DNA
<213> ORGANISM: Homo sapiens

<400> SEQUENCE: 5

```
cctccaagga cctactgtgt gccgggcatg gggacgtcaa agcacaggga gctataaggg    60
aggtagttgg agcaccacgg gagcctgggg tgtggggtgg gagcaggggc ggggctcctg   120
ggccatgcag atggggttgg catggggttg ggaggggcc cacggaggct tctggactct    180
gagtgtggag ccaggggcag cagggctgtc tctgaactcc caggcttgtg tttgagcaaa   240
ggaattctct ccccctccct ctcccctcgg ggcgggcccg agcctccagc tataaactcc   300
ccggagcttc agtgccctca gcaaggctca gcctcaagat tcacagca               348
```

<210> SEQ ID NO 6
<211> LENGTH: 348
<212> TYPE: DNA
<213> ORGANISM: Homo sapiens

<400> SEQUENCE: 6

```
cctccaagga cctactgtgt gccgggcatg gggacgtcaa agcacaggga gctataaggg    60
aggtagttgg agcaccacgg gagcctgggg tgtggggtgg gagcaggggc ggggctcctg   120
ggccatgcag atggggttgg catggggttg ggaggggcc cacggaggct tctggactct    180
gagtgtggag ccaggggcag cagggctgtc tctgaactcc caggcttgtg tttgagcaaa   240
ggaattctct ccccctccct ctcccctcgg ggcgggcccg agcctccagc tataaacttc   300
ccggagcttc tgtgccctca gcaaggctca gcctcaagat tcacagca               348
```

<210> SEQ ID NO 7
<211> LENGTH: 910
<212> TYPE: DNA
<213> ORGANISM: Homo sapiens

<400> SEQUENCE: 7

```
aaataccaca agatgcatag aaggaagtgc aaagaaagga gaaagagag acagagatat     60
actcacagca aggtgcagag acatggagac cctataagag atggaaatgg agagccacag   120
aggggggaact gcgggcacta agagagacat ggagagaact agaaagatag agacgtgaac  180
acagacacag agacccagag ccaaaaagag acagaaatgg ggtcataggt ggacagaaat   240
gcacagagag actgtgagcc cccacagaca caaacgctga gaggggcaga catgcagaga   300
cacccacaga aatgcagaga caaaaccacc cggagacaca tgccgagaaa cacactgagg   360
ggctcagaaa gcgacagatg cagagagagc ccaagacaga cccagcaagg ggccccgaga   420
aatgcacaga aacacaaaga ccgagaccac cagagacaga ggtacggaga ggcggggagg   480
gtgaggaagc ctgctctcca gggctggctt gaacctagaa ctcaaggtca tggcttggct   540
gggaagcggg aggggatac caaaaaagat cagcgttaga tggaggtggg gagggagggt    600
aggtttcacc ctaattgaca ccccaccctc cccctccccc tccccacacc tgcttcccgg    660
ctttagtgcc tgttgtcacc aggatggaat cctggcggca gacaaagggg tggggtggg    720
aggaggagac aaaaagatgg acagagacag aggaggagac taagaagtag agacagacac    780
acagagacac acagatggag agccacagag acaacagaaa tggggtccaa gaaagagacc    840
tagatagaaa gagggaacag agagaagaaa acaggaaaca ttccttatag cccatgtgtc    900
attagtaggt                                                         910
```

<210> SEQ ID NO 8
<211> LENGTH: 861
<212> TYPE: DNA
<213> ORGANISM: Homo sapiens

```
<400> SEQUENCE: 8
gaaaacttag agtgccatta tctggggtat catgaactgg gcctccgagt ttgggtatca      60
agattttggg ggtctcatat tcttgaggtt tcagatttta ggaggtctca agacctgggg     120
gtggtcttag gatgtcccgg cccatatctg gactatcaag aactgggatt tcagaatcca     180
gagctgtgag gacttgctgg cctcagaaac acgggcatca taaatcgggg tctcagaatc     240
tgtgggtatt gggatttggg gctaggcacc ctgtggccta gggtgtctca aagactttga     300
ggtctaagaa tgtaggggtc agggtgaggt ctacggacag aaggtgccct ttatgcccct     360 gcccctacg tgatgtatgg gaaggtgaaa ggggagacag gtggggagga aaccagccag     420
tggggtgggg cgagtgggag aggggatgcg ggtgactaat tctcccagaa gccccccttc     480
ctcaaatccc ttcttaggaa atgtcctcgg tttcaccatc tatgacatcc ccccaaaata     540
gctcctgggg gtggggcagc tattgtcttc aggccactgt cccttctcaa atgcctcttc     600
ctaatcccaa ctggatcagg ttcccatgga cttgtcataa gacaaaagag gacagctgtg     660 ctgaggggc agggtctgca gcctcctggc tgtgccagga ccacacctac caaggtctgt      720
cctcatgcat gctttaggac agccggcccc ctccctcaga cccaagagtc cagacctgag     780
ccctcctccc tcagacgcag gagtacaggc ccccagcccg ctcctccctc agactcagga     840
gtctagactc ccagcctctc c                                               861

<210> SEQ ID NO 9
<211> LENGTH: 868
<212> TYPE: DNA
<213> ORGANISM: Homo sapiens

<400> SEQUENCE: 9
gtaaccgcgg ctgcttcgct tcccgagacc gatgtcgggg gcccggggg accccgata       60 tcctcgggcc ccaacctcca agaccaccct tccctccctc cgccccata acccgccccc      120 aggcccggtc ctttaagccc ctgagagctc ctgcgccctc tcggggccgg gaagggaaat     180
ggccccgcag tggctttaac cctttccctt ccttcttaaa gggaccgaca cccaagcctt     240 cttcccccagt ctggaggaat cttttacagaa gggttggatg tttgcggaga agcaccaccc  300
catcccccct tatcttcgcc tccaaccttg tctgttattt tctccccat atacattcaa     360 aggttgggc ttggaattta ggattgcaga ggaggcgagc gctgggagtc agggtctcca      420
aggtcgggcc gggggcgggg gggcggtggg gcggtgggca gggggcgagc tggggagaga    480
gcgctggggt cactgaatga agacagaggt tgggaccccc tgcactgctg ggtcctaatg     540
gaggagagca ggagctctgg gcatataaat agagaaaggt ctgggggttt gcactcctgg    600
gtgtgcagac agtgggggtg gggggtcccc acaccagttc tgaatgtata tctgatgcgt    660
gtgaccctct tcctccttta cagccaccct gactttcctt ccctcttttc ttctccccat    720
cccccctcct ccagaactgg actccagagt ccttccctgg ggtcctgggg gccgaggctt    780
ggggggtccc tccccagggt gtgtcaggcc tagcccctct cctctaaact cttgctaatt    840 atctctttt atcccccacc accaacag                                         868
```

TNNT1 MINI-PROMOTERS

FIELD OF THE INVENTION

The invention relates to gene promoters and regulatory elements. More specifically, the invention relates to novel TNNT1 promoter compositions and related methods.

BACKGROUND

The troponin T type 1 (skeletal, slow) muscle protein is encoded by the TNNT1 gene. The protein encoded by the TNNT1 gene is a subunit of troponin and is involved in striated muscle contraction. Mutations in the TNNT1 gene have been shown to cause nemaline myopathy that is characterized by muscle weakness and respiratory insufficiency (Johnston et al. 2000; van der Pol et al. 2014). In the brain, TNNT1 is expressed in sagittal sections of the thalamus, the Islands of Calleja and the superficial grey layer of superior colliculus. Transcripts of the TNNT1 gene have also been detected in the murine heart (Pinto et al. 2012; Manuylov et al. 2009) and in human and murine skeletal muscle (Sabry et al. 1991; Kee and Hardeman 2008; Johnston et al. 2000).

There is a need for characterized human TNNT1 promoters for gene expression, for instance in human gene therapy applications. It is particularly useful to identify small promoter elements that are sufficient to drive expression in regions of the brain, for instance in thalamus, the Islands of Calleja and the superficial grey layer of superior colliculus as well as in the heart and striated muscle. Such small promoter elements, or "mini-promoters" are particularly useful in certain applications, for instance they are more amenable to insertion into viral vectors used in gene therapy applications.

TNNT1 promoter elements and gene expression described in the art, including:

de Leeuw C N, Dyka F M, Boye S L, Laprise S, Zhou M, Chou A Y, Borretta L, McInerny S C, Banks K G, Portales-Casamar E, et al. 2014. Targeted CNS delivery using human MiniPromoters and demonstrated compatibility with adeno-associated viral vectors. *Molecular Therapy Methods & Clinical Development* 1: e5.

Johnston J J, Kelley R I, Crawford T O, Morton D H, Agarwala R, Koch T, Schäffer A A, Francomano C A, Biesecker L G. 2000. A novel nemaline myopathy in the Amish caused by a mutation in troponin T1. *Am J Hum Genet* 67: 814-821.

Kee A J, Hardeman E C. 2008. Tropomyosins in skeletal muscle diseases. *Adv Exp Med Biol* 644: 143-157.

Manuylov N L, Tevosian S G. 2009. Cardiac expression of Tnnt1 requires the GATA4-FOG2 transcription complex. *The Scientific World JOURNAL* 9: 575-587.

Lowe X R, Lu X, Marchetti F, Wyrobek A J. 2007. The expression of Troponin T1 gene is induced by ketamine in adult mouse brain. Brain Res 1174:7-17

SUMMARY OF THE INVENTION

The present invention provides novel nucleic acid sequence compositions and methods relating to minimal human TNNT1 promoters. The invention is based in part on the surprising discovery that certain minimal TNNT1 promoter elements are capable of expressing in specific cell types, for instance in cells of the brain.

In one embodiment of the invention, there is provided an isolated nucleic acid fragment comprising a TNNT1 mini-promoter, wherein the TNNT1 mini-promoter comprises a TNNT1 regulatory element operably linked in a non-native conformation to a TNNT1 basal promoter. The TNNT1 mini-promoter may have a nucleic acid sequence which is substantially similar in sequence and function to SEQ ID NO: 1-4. The TNNT1 basal promoter may have a nucleic acid sequence which is substantially similar in sequence and function to SEQ ID NO: 5 or 6. The TNNT1 regulatory element may have a nucleic acid sequence which is substantially similar in sequence and function to SEQ ID NO: 7-9. In other embodiments, there is provided an isolated nucleic acid fragment comprising a TNNT1 mini-promoter, wherein the TNNT1 mini-promoter comprises a TNNT1 basal promoter. The TNNT1 basal promoter may have a nucleic acid sequence which is substantially similar in sequence and function to SEQ ID NO: 5 or 6. The TNNT1 mini-promoters may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule.

In one embodiment, there is provided an expression vector comprising a TNNT1 mini-promoter, wherein the TNNT1 mini-promoter comprises a TNNT1 regulatory element operably linked in a non-native conformation to a TNNT1 basal promoter. The TNNT1 mini-promoter may have a nucleic acid sequence which is substantially similar in sequence and function to SEQ ID NO: 1-4. The TNNT1 basal promoter may have a nucleic acid sequence which is substantially similar in sequence and function to SEQ ID NO: 5 or 6. The TNNT1 regulatory element may have a nucleic acid sequence which is substantially similar in sequence and function to SEQ ID NO: 7-9. In other embodiments, there is provided an expression vector comprising a TNNT1 mini-promoter, wherein the TNNT1 mini-promoter comprises a TNNT1 basal promoter. The TNNT1 basal promoter may have a nucleic acid sequence which is substantially similar in sequence and function to SEQ ID NO: 5 or 6. The TNNT1 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may further comprise a genomic targeting sequence. The genomic targeting sequence may be HPRT.

In one embodiment, there is provided a method for expressing a gene, protein, RNA interference molecule or the like in a cell, the method comprising introducing into the cell an expression vector comprising a TNNT1 mini-promoter element, wherein the TNNT1 mini-promoter element comprises a TNNT1 regulatory element operably linked in a non-native conformation to a TNNT1 basal promoter element. In another embodiment, the TNNT1 mini-promoter comprises a TNNT1 basal promoter. Cells of interest include, without limitation, cells of the peripheral or central nervous system and progenitors thereof, e.g. embryonic stem cells, neural stem cells, neurons, glial cells, astrocytes, microgial cells, etc., or cells of striated, cardiac or smooth muscle throughout the body and progenitors thereof, e.g. satellite cells, cardiomyocytes, myocytes, myoblasts, etc. The TNNT1 mini-promoter may have a nucleic acid sequence which is substantially similar in sequence and function to SEQ ID NO: 1-4. The TNNT1 regulatory element may have a nucleic acid sequence which is substantially similar in sequence and function to SEQ ID NO: 7-9. The TNNT1 basal promoter may have a nucleic acid sequence which is substantially similar in sequence and function to SEQ ID NO: 5 or 6. The TNNT1 mini-promoter may further be operably linked to an expressible sequence, e.g. reporter genes, genes encoding a polypeptide of interest, regulatory RNA sequences such as miRNA, siRNA, antisense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may thus further comprise a genomic targeting sequence. The genomic targeting sequence may be HPRT.

In one embodiment of the invention, there is provided a method for identifying or labeling a cell, the method comprising introducing into the cell an expression vector comprising a TNNT1 mini-promoter element, wherein the TNNT1 mini-promoter element comprises a TNNT1 regulatory element operably linked in a non-native conformation to a TNNT1 basal promoter element, and wherein the expressible sequence comprises a reporter gene. In other embodiments, the TNNT1 mini-promoter comprises a TNNT1 basal promoter. The TNNT1 mini-promoter element may have a nucleic acid sequence substantially similar in sequence and function to SEQ ID NO: 1-4. The TNNT1 regulatory element may have a nucleic acid sequence substantially similar in sequence and function to SEQ ID NO: 7-9. The TNNT1 basal promoter element may have a nucleic acid sequence substantially similar in sequence and function to SEQ ID NO: 5 or 6. In some embodiments, the cell is a peripheral or central nervous system cell or progenitors thereof, including, without limitation, embryonic stem cells, neural stem cells, glial cells, astrocytes, neurons and the like etc, or cells of striated, cardiac or smooth muscle throughout the body and progenitors thereof, e.g. satellite cells, cardiomyocytes, myocytes, myoblasts, and the like etc. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In one embodiment of the invention, there is provided a method for monitoring or tracking the development or maturation of a cell, the method comprising: 1) introducing into the cell a expression vector comprising a TNNT1 mini-promoter element operably linked to an expressible sequence, wherein the TNNT1 mini-promoter element comprises a TNNT1 regulatory element operably linked in a non-native conformation to a TNNT1 basal promoter element, and wherein the expressible sequence comprises a reporter gene; and 2) detecting the expression of the reporter gene in the cell of in progeny of the cell as a means of determining the lineage, identity or developmental state of the cell or cell progeny. In other embodiments, the TNNT1 mini-promoter comprises a TNNT1 basal promoter. The TNNT1 mini-promoter element may have a nucleic acid sequence substantially similar in sequence and function to SEQ ID NO: 1-4. The TNNT1 regulatory element may have a nucleic acid sequence substantially similar in sequence and function to SEQ ID NO: 7-9. The TNNT1 basal promoter element may have a nucleic acid sequence substantially similar in sequence and function to SEQ ID NO: 5 or 6. In some embodiments, the cell is a peripheral or central nervous system cell or progenitors thereof, including, without limitation, embryonic stem cells, neural stem cells, glial cells, neurons and the like, or cells of striated, cardiac or smooth muscle throughout the body and progenitors thereof, including, without limitation, satellite cells, cardiomyocytes, myocytes, myoblasts and the like.

In certain embodiments of the invention, there is thus provided a method of treatment of a subject having a disease involving the hypothalamus or thalamus in the brain, or alternatively in muscle throughout the body, including skeletal muscle and heart muscle, the method comprising administering to the subject a therapeutically effective dose of a composition comprising a TNNT1 mini-promoter element, wherein the TNNT1 mini-promoter element comprises a TNNT1 regulatory element operably linked in a non-native conformation to a TNNT1 basal promoter element. In another embodiment, the TNNT1 mini-promoter comprises a TNNT1 basal promoter. The TNNT1 mini-promoter element may have a nucleic acid sequence substantially similar in sequence and function to SEQ ID NO: 1-4. The TNNT1 regulatory element may have a nucleic acid sequence substantially similar in sequence and function to SEQ ID NO: 7-9. The TNNT1 basal promoter element may have a nucleic acid sequence substantially similar in sequence and function to SEQ ID NO: 5 or 6. The disease or condition may be chosen from: hypothalamus or thalamus related brain disorders, nemaline myopathies, muscular dystrophies, heart failure or defects, or other muscle-related disorders.

BRIEF DESCRIPTION OF FIGURES

The patent or application file contains at least one drawing executed in color. Copies of this patent or patent application publication with color drawing(s) will be provided by the Office upon request and payment of the necessary fee.

(FIG. 2A) Ple232 expressed in the anterior cingulate and zona incerta (top panel, arrow and arrow head, respectively) and in the lateral hippocampus (bottom panel, arrow). (FIG. 2B) Ple232 stained strongly in skeletal muscle and the tongue of the embryo but was not visible in the brain or spinal cord (top panel, whole mount stained embryo; bottom panel, partially cleared embryo to enhance visualization). Note that some weak expression was detected in the heart (bottom panel, arrow). Ctx, cortex; Hipp, hippocampus; RRs, regulatory regions. Figure modified from (de Leeuw et al. 2014).

FIG. 3A-3B—The Ple301 construct expresses in skeletal muscle and in the heart. The Ple301 promoter driving icre expression was constructed and ssAAV9 virus generated (vEMS48). P0 mice were injected intravenously with virions and mice were harvested at P21 and P56 via perfusion and stained overnight for lacZ activity (blue), indicative of promoter activity. (FIG. 3A) Quadriceps muscle (both at P21 and P56) was cut in half with a razor blade and demonstrates clear staining of the striated multi-nucleated muscle fibers. (FIG. 3B) The heart is positive for lacZ staining at both P21 and P56. P, post-natal day. RR, regulatory regions.

DETAILED DESCRIPTION

Figure 1:
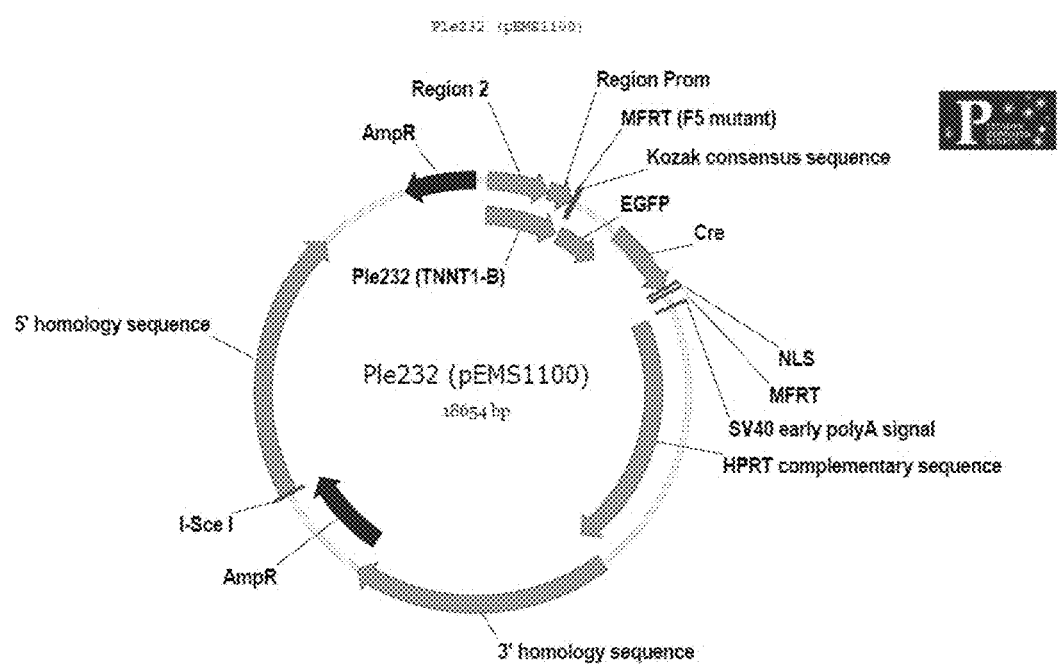
FIG. 1—DNA expression vector (pEMS1100) into which TNNT1 promoter elements were inserted for expression studies. The TNNT1 promoter with a nucleic acid sequence corresponding to SEQ ID NO: 1 was inserted into the multiple cloning site (MCS) of the pEMS1100 vector such that it became operably linked to the lacZ reporter gene also contained the HPRT genomic targeting sequence, an ampicillin resistance gene (AmpR) for screening, and a transcriptional termination sequence (SV40 polyA), as well as other elements necessary for vector replication and gene expression.

The compositions of the present invention include novel polynucleotides comprising TNNT1 promoter elements (also referred to herein as TNNT1 mini-promoters) as well as novel expression vectors comprising said TNNT1 promoter elements (or mini-promoters). The present invention also includes various methods utilizing these novel TNNT1 promoter (or mini-promoter) elements or expression vectors.

The term TNNT1' refers to the gene which encodes the TNNT1 protein, other aliases include the Skeletal muscle-specific troponin T (sTnT) or the Human slow skeletal troponin T (HSSTnT). The human homolog of TNNT1 is encoded by the human gene identified as EntrezGene #7138 and is located on chromosome 19 at location 19q13.4. There also three separate isoform encoded by human TNNT1 gene due to splicing variants, these are identified as the Protein Accession NP_003274 (troponin T, slow skeletal muscle isoform a), the Protein Accession NP_001119604 (troponin T, slow skeletal muscle isoform b) and the Protein Accession NP_001119605 (troponin T, slow skeletal muscle isoform c), however other protein accession numbers may also be assigned to this protein. TNNT1 may also include other isoforms and/or splice variants. Other mammalian TNNT1 homologs may include but are not limited to: *Rattus norvegicus* (EntrezGene #171409), *Mus musculus* (EntrezGene #21955), Pan troglodytes (EntrezGene #735354), *Macaca mulatta* (EntrezGene #698339).

The term 'promoter' refers to the regulatory DNA region which controls transcription or expression of a gene and which can be located adjacent to or overlapping a nucleotide or region of nucleotides at which RNA transcription is initiated. A promoter contains specific DNA sequences which bind protein factors, often referred to as transcription factors, which facilitate binding of RNA polymerase to the DNA leading to gene transcription. A 'basal promoter', also referred to as a 'core promoter', usually means a promoter which contains all the basic necessary elements to promote transcriptional expression of an operably linked polynucleotide. Eukaryotic basal promoters typically, though not necessarily, contain a TATA-box and/or a CAAT box. A 'TNNT1 basal promoter', in the context of the present invention and as used herein, is a nucleic acid compound having a sequence with at least 65%, at least 70%, at least 80%, at least 85%, at least 90%, at least 95%, or at least 99% similarity to SEQ ID NO: 5 or 6.

A promoter may also include 'regulatory elements' that influence the expression or transcription by the promoter. Such regulatory elements encode specific DNA sequences which bind other factors, which may include but are not limited to enhancers, silencers, insulators, and/or boundary elements. A 'TNNT1 regulatory element', in the context of the present invention and as used herein, is a nucleic acid compound having a sequence with at least 65%, at least 70%, at least 80%, at least 85%, at least 90%, at least 95%, or at least 99% similarity to SEQ ID NO: 4 or 5. The present invention provides, in certain embodiments as described herein, different promoters of the TNNT1 gene. In some embodiments, the TNNT1 promoter comprises a TNNT1 regulatory element operably linked to a TNNT1 basal promoter.

The term 'operably linked', in the context of the present invention, means joined in such a fashion as to work together to allow transcription. In some embodiments of the invention, two polynucleotide sequences may be operably linked by being directly linked via a nucleotide bond. In this fashion, the two operably linked elements contain no intervening sequences and in being joined are able to direct transcription of an expression sequence. In other embodiments of the invention, two elements may be operably linked by an intervening compound, for instance a polynucleotide sequence of variable length. In such a fashion, the operably linked elements, although not directly juxtaposed, are still able to direct transcription of an expression sequence. Thus, according to some embodiments of the invention, one or more promoter elements may be operably linked to each other, and additionally be operably linked to a downstream expression sequence, such that the linked promoter elements are able to direct expression of the downstream expression sequence.

The term 'mini-promoter' refers to a promoter in which certain promoter elements are selected from an endogenous full length promoter for a gene, usually in such a fashion as to reduce the overall size of the promoter compared to the native sequence. For example, after identification of critical promoter elements, using one or more of various techniques, the native sequences that intervene between identified elements may be partially or completely removed. Other non-native sequences may optionally be inserted between the identified promoter elements. Promoter sequences such as enhancer elements may have an orientation that is different from the native orientation—for example, a promoter element may be inverted, or reversed, from its native orientation. Alternatively, selecting a minimal basal promoter that is sufficient to drive expression in particular cells or tissues may also be desirable. Since promoter elements that impact expression patterns are known to be distributed over varying distances of the proximal and/or distal endogenous promoter, it is a non-trivial task to identify a mini-promoter comprising a minimal basal promoter and optional regulatory regions that will adequately express in the desired cell or tissue types. A mini-promoter may provide certain advantages over native promoter conformations. For example, the smaller size of the mini-promoter may allow easier genetic manipulation, for example in the design and/or construction of expression vectors or other recombinant DNA constructs. In addition, the smaller size may allow easier insertion of DNA constructs into host cells and/or genomes, for example via transfection, transformation, etc. Other advantages of mini-promoters are apparent to one of skill in the art. In some embodiments of the invention, there are thus provided novel TNNT1 mini-promoters comprising a TNNT1 regulatory element operably linked in a non-native conformation to a TNNT1 basal promoter. In general the spacing between the TNNT1 regulatory element and the TNNT1 basal promoter is not more than about 15 KB, generally not more than about 10 KB, usually not more than about 1 KB, more often not more than about 500 nt, and may be not more than about 100 nt, down to a direct joining of the two sequences. In other embodiments, there is provided a minimal TNNT1 basal promoter.

The term 'expressible sequence' refers to a polynucleotide composition which is operably linked to a promoter element such that the promoter element is able to cause transcriptional expression of the expression sequence. An expressible sequence is typically linked downstream, on the 3'-end of the promoter element(s) in order to achieve transcriptional expression. The result of this transcriptional expression is the production of an RNA macromolecule. The expressed RNA molecule may encode a protein and may thus be subsequently translated by the appropriate cellular machinery to produce a polypeptide protein molecule. In some embodiments of the invention, the expression sequence may encode a reporter protein. Alternately, the RNA molecule may be an antisense, RNAi or other non-coding RNA molecule, which may be capable of modulating the expression of specific genes in a cell, as is known in the art.

The term 'RNA' as used in the present invention includes full-length RNA molecules, which may be coding or non-coding sequences, fragments, and derivatives thereof. For example, a full-length RNA may initially encompass up to about 20 Kb or more of sequence, and frequently will be processed by splicing to generate a small mature RNA. Fragments, RNAi, miRNA and anti-sense molecules may be smaller, usually at least about 18 nt. in length, at least about 20 nt in length, at least about 25 nt. in length, and may be up to about 50 nt. in length, up to about 100 nt in length, or more. RNA may be single stranded, double stranded, synthetic, isolated, partially isolated, essentially pure or recombinant. RNA compounds may be naturally occurring, or they may be altered such that they differ from naturally occurring RNA compounds. Alterations may include addition, deletion, substitution or modification of existing nucleotides. Such nucleotides may be either naturally occurring, or non-naturally occurring nucleotides. Alterations may also involve addition or insertion of non-nucleotide material, for instance at the end or ends of an existing RNA compound, or at a site that is internal to the RNA (ie. between two or more nucleotides).

The term 'nucleic acid' as used herein includes any nucleic acid, and may be a deoxyribonucleotide or ribonucleotide polymer in either single or double-stranded form. A 'polynucleotide' or 'nucleotide polymer' as used herein may include synthetic or mixed polymers of nucleic acids, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e. g., phosphorothioates, phosphorodithioates, etc.), pendent moieties (e.g., polypeptides), and modified linkages (e.g., alpha anomeric polynucleotides, etc.). Also included are synthetic molecules that mimic polynucleotides in their ability to bind to a designated sequence via hydrogen bonding and other chemical interactions.

A 'purine' is a heterocyclic organic compound containing fused pyrimidine and imidazole rings, and acts as the parent compound for purine bases, adenine (A) and guanine (G). 'Nucleotides' are generally a purine (R) or pyrimidine (Y) base covalently linked to a pentose, usually ribose or deoxyribose, where the sugar carries one or more phosphate groups. Nucleic acids are generally a polymer of nucleotides joined by 3' 5' phosphodiester linkages. As used herein 'purine' is used to refer to the purine bases, A and G, and more broadly to include the nucleotide monomers, deoxyadenosine-5'-phosphate and deoxyguanosine-5'-phosphate, as components of a polynucleotide chain. A 'pyrimidine' is a single-ringed, organic base that forms nucleotide bases, such as cytosine (C), thymine (T) and uracil (U). As used herein 'pyrimidine' is used to refer to the pyrimidine bases, C, T and U, and more broadly to include the pyrimidine nucleotide monomers that along with purine nucleotides are the components of a polynucleotide chain.

It is within the capability of one of skill in the art to modify the sequence of a promoter nucleic acid sequence, e.g. the provided basal promoter and regulatory sequences, in a manner that does not substantially change the activity of the promoter element, i.e. the transcription rate of an expressible sequence operably linked to a modified promoter sequence is at least about 65% the transcription rate of the original promoter, at least about 75% the transcription rate of the original promoter sequence, at least about 80%, at least about 90%, at least about 95%, at least about 99%, or more. Such modified sequences would be considered to be 'functionally similar' or to have 'functional similarity' or 'substantial functional similarity' to the unmodified sequence. Such modifications may include insertions, deletions which may be truncation of the sequence or internal deletions, or substitutions. The level of sequence modification to an original sequence will determine the 'sequence similarity' of the original and modified sequences. Modification of the promoter elements of the present invention in a fashion that does not significantly alter transcriptional activity, as described above would result in sequences with 'substantial sequence similarity' to the original sequence i.e. the modified sequence has a nucleic acid composition that is at least about 65% similar to the original promoter sequence, at least about 75% similar to the original promoter sequence, at least about 80%, at least about 90%, at least about 95%, at least about 99%, or more similar to the original promoter sequence. Thus, mini-promoter elements which have substantial functional and/or sequence similarity are herein described and are within the scope of the invention.

An 'RNA interference molecule', or 'RNA interference sequence' as defined herein, may include, but is not limited to, an antisense RNA molecule, a microRNA molecule or a short hairpin RNA (shRNA) molecule. Typically, RNA interference molecules are capable of target-specific modulation of gene expression and exert their effect either by mediating degradation of the mRNA products of the target gene, or by preventing protein translation from the mRNA of the target gene. The overall effect of interference with mRNA function is modulation of expression of the product of a target gene. This modulation can be measured in ways which are routine in the art, for example by Northern blot assay or reverse transcriptase PCR of mRNA expression, Western blot or ELISA assay of protein expression, immunoprecipitation assay of protein expression, etc.

An 'antisense RNA molecule', as used herein, is typically a single stranded RNA compound which binds to complementary RNA compounds, such as target mRNA molecules, and blocks translation from the complementary RNA compounds by sterically interfering with the normal translational machinery. Specific targeting of antisense RNA compounds to inhibit the expression of a desired gene may design the antisense RNA compound to have a homologous, complementary sequence to the desired gene. Perfect homology is not necessary for inhibition of expression. Design of gene specific antisense RNA compounds, including nucleotide sequence selection and additionally appropriate alterations, are known to one of skill in the art.

The term 'microRNA molecule', 'microRNA' or 'miRNA', as used herein, refers to single-stranded RNA molecules, typically of about 21-23 nucleotides in length, which are capable of modulating gene expression. Mature miRNA molecules are partially complementary to one or more messenger RNA (mRNA) molecules, and their main function is to downregulate gene expression. Without being bound by theory, miRNAs are first transcribed as primary transcripts or pri-miRNA with a cap and poly-A tail and processed to short, 70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end. The remaining strand, known as the anti-guide or passenger strand, is degraded as a RISC complex substrate. After integration into the active RISC complex, miRNAs base pair with their complementary mRNA molecules and induce mRNA degradation by argonaute proteins, the catalytically active members of the RISC complex. Animal miRNAs are usually complementary to a site in the 3' UTR whereas plant miRNAs are usually complementary to coding regions of mRNAs.

The term 'short hairpin RNA' or 'shRNA' refers to RNA molecules having an RNA sequence that makes a tight hairpin turn that can be used to silence gene expression via RNA interference. The shRNA hairpin structure is cleaved by the cellular machinery into siRNA, which is then bound to the RNA-induced silencing complex (RISC). This complex binds to and cleaves mRNAs which match the siRNA that is bound to it. shRNA is transcribed by RNA Polymerase III whereas miRNA is transcribed by RNA Polymerase II. Techniques for designing target specific shRNA molecules are known in the art.

An 'expression vector' is typically a nucleic acid molecule which may be integrating or autonomous, (i.e. self-replicating), and which contains the necessary components to achieve transcription of an expressible sequence in a target cell, when introduced into the target cell. Expression vectors may include plasmids, cosmids, phage, YAC, BAC, mini-chromosomes, viruses, e.g. retroviruses, adenovirus, lentivirus, SV-40, and the like; etc. Many such vectors have been described in the art and are suitable for use with the promoters of the present invention. Expression vectors of the present invention include a promoter as described herein, operably linked to an expressible sequence, which may also be optionally operably linked to a transcription termination sequence, such as a polyadenylation sequence. The expression vector optionally contains nucleic acid elements which confer host selectivity, elements that facilitate replication of the vector, elements that facilitate integration of the vector into the genome of the target cell, elements which confer properties, for example antibiotic resistance, to the target cell which allow selection or screening of transformed cells and the like. Techniques and methods for design and construction of expression vectors are well known in the art.

It may be desirable, when driving expression of an expressible sequence with a particular promoter system to have the expression occur in a stable and consistent manner. A factor that has been shown to affect expression is the site of integration of an expression vector or construct into the genome of the target cell, sometimes called 'position effects'. Such position effects may be caused by, for example, local chromatin structure which affects expression of sequences from that region of the genome. One method to control for position effects when integrating an expression vector or construct into the genome of a target cell is to include a 'genomic targeting sequence' in the vector or construct that directs integration of the vector or construct to a specific genomic site. As an example, the hypoxanthine phosphoribosyltransferase (HPRT) gene has been used successfully for this purpose (Bronson, Plaehn et al. 1996; Jasin, Moynahan et al. 1996). The HPRT gene has additional advantages as a genomic targeting sequence, for instance its concomitant use as a selectable marker system. Other genomic targeting sequences that may be useful in the present invention are described in the art, for instance (Jasin, Moynahan et al. 1996; van der Weyden, Adams et al. 2002). The genomic targeting signals as described herein are useful in certain embodiments of the present invention.

Introduction of nucleic acids or expression vectors into cells may be accomplished using techniques well known in the art, for example microinjection, electroporation, particle bombardment, or chemical transformation, such as calcium-mediated transformation, as described for example in Maniatis et al. 1982, Molecular Cloning, A laboratory Manual, Cold Spring Harbor Laboratory or in Ausubel et al. 1994, Current protocols in molecular biology, Jolm Wiley and Sons.

In certain embodiments of the invention, there are provided methods of treatment using the nucleic acids or expression vectors, for instance for gene therapy applications. The nucleic acids or expression vectors of the present invention may be administered in isolation, or may be linked to or in combination with tracer compounds, liposomes, carbohydrate carriers, polymeric carriers or other agents or excipients as will be apparent to one of skill in the art. In an alternate embodiment, such compounds may comprise a medicament, wherein such compounds may be present in a pharmacologically effective amount.

The term 'medicament' as used herein refers to a composition that may be administered to a patient or test subject and is capable of producing an effect in the patient or test subject. The effect may be chemical, biological or physical, and the patient or test subject may be human, or a non-human animal, such as a rodent or transgenic mouse, or a dog, cat, cow, sheep, horse, hamster, guinea pig, rabbit or pig. The medicament may be comprised of the effective chemical entity alone or in combination with a pharmaceutically acceptable excipient.

The term 'pharmaceutically acceptable excipient' may include any and all solvents, dispersion media, coatings, antibacterial, antimicrobial or antifungal agents, isotonic and absorption delaying agents, and the like that are physiologically compatible. An excipient may be suitable for intravenous, intraperitoneal, intramuscular, subcutaneous, intrathecal, intraocular, topical or oral administration. An excipient may include sterile aqueous solutions or dispersions for extemporaneous preparation of sterile injectable solutions or dispersion. Use of such media for preparation of medicaments is known in the art.

The nucleic acids or expression vectors of the present invention may be administered to a subject using a viral delivery system. For instance, the nucleic acids may be inserted into a viral vector using well known recombinant techniques. The subsequent viral vector may then be packaged into a virus, such as adenovirus, lentivirus, attenuated virus, adeno-associated virus (AAV), and the like. Viral delivery for gene therapy applications is well known in the art. There exist a variety of options for viruses suitable for such delivery, which may also involve selecting an appropriate viral serotype for delivery and expression in an appropriate tissue.

Compositions or compounds according to some embodiments of the invention may be administered in any of a variety of known routes. Examples of methods that may be suitable for the administration of a compound include orally, intravenous, inhalation, intramuscular, subcutaneous, topical, intraperitoneal, intra-ocular, intra-rectal or intra-vaginal suppository, sublingual, and the like. The compounds of the present invention may be administered as a sterile aqueous solution, or may be administered in a fat-soluble excipient, or in another solution, suspension, patch, tablet or paste format as is appropriate. A composition comprising the compounds of the invention may be formulated for administration by inhalation. For instance, a compound may be combined with an excipient to allow dispersion in an aerosol. Examples of inhalation formulations will be known to those skilled in the art. Other agents may be included in combination with the compounds of the present invention to aid uptake or metabolism, or delay dispersion within the host, such as in a controlled-release formulation. Examples of controlled release formulations will be known to those of skill in the art, and may include microencapsulation, embolism within a carbohydrate or polymer matrix, and the like. Other methods known in the art for making formulations are found in, for example, "Remington's Pharmaceutical Sciences", (19th edition), ed. A. Gennaro, 1995, Mack Publishing Company, Easton, Pa.

The dosage of the compositions or compounds of some embodiments of the invention may vary depending on the route of administration (oral, intravenous, inhalation, or the like) and the form in which the composition or compound is administered (solution, controlled release or the like). Determination of appropriate dosages is within the ability of one of skill in the art. As used herein, an 'effective amount', a 'therapeutically effective amount', or a 'pharmacologically effective amount' of a medicament refers to an amount of a medicament present in such a concentration to result in a therapeutic level of drug delivered over the term that the drug is used. This may be dependent on mode of delivery, time period of the dosage, age, weight, general health, sex and diet of the subject receiving the medicament. Methods of determining effective amounts are known in the art. It is understood that it could be potentially beneficial to restrict delivery of the compounds of the invention to the target tissue or cell in which protein expression. It is also understood that it may be desirable to target the compounds of the invention to a desired tissue or cell type. The compounds of the invention may thus be coupled to a targeting moiety. The compounds of the invention may be coupled to a cell uptake moiety. The targeting moiety may also function as the cell uptake moiety.

TNNT1 Mini-Promoters

The present invention herein provides novel TNNT1 mini-promoter sequences which are capable of effecting transcriptional expression in a spatial and temporal fashion in the brain and in the muscle. Certain TNNT1 mini-promoters of the invention comprise minimal TNNT1 promoter elements joined in a non-native configuration, thus providing advantageous characteristics. Other TNNT1 mini-promoters of the invention comprise a minimal TNNT1 basal promoter. Also provided are novel expression vector compositions comprising TNNT1 mini-promoters which allow consistent specific spatiotemporal transcription of expression sequences. Also provided are novel methods utilizing these TNNT1 mini-promoters and expression vectors.

The TNNT1 promoters of the invention, as described herein, are referred to as 'mini-promoters' to reflect the fact that the mini-promoters comprise minimal TNNT1 promoter elements sufficient to drive expression, and that may also be joined by non-native sequences. In this context, the native intervening sequences may have been partially or completely removed, and optionally may have been replaced with non-native sequences. Furthermore, the natural spatial arrangement of elements may be altered, such that downstream promoter elements (in natural conformation) are moved upstream (in non-native conformation). In such a fashion, the natural spacing of the promoter elements, for instance a human TNNT1 regulatory element corresponding to SEQ ID NO: 7-9 and the human TNNT1 basal promoter elements corresponding to SEQ ID NO: 5 or 6 or sequences with substantial functional and/or sequence equivalence, is altered. Additionally, the orientation of the different promoter elements may be altered—for instance the regulatory element corresponding to SEQ ID NO: 7-9 may be inverted relative to the basal promoter element corresponding to SEQ ID NO: 5 or 6. An advantage of such non-native mini-promoters is that the removal of native intervening sequences reduces the size of the mini-promoter while maintaining the functional activity of the promoter, thus improving the utility of the mini-promoter for various applications. Furthermore, the inversion of an enhancer/promoter element may allow retention of the enhancer properties without causing alternate promoter activity.

The inventors have demonstrated, as illustrated in the non-limiting Working Examples, that human TNNT1 mini-promoters having a sequence corresponding to SEQ ID NO: 1 and 2 (also referred to in the Working Examples as Ple232 and Ple301), and which is comprised of one or more human TNNT1 regulatory elements (for Ple232 and Ple301 the regulatory element is SEQ ID NO: 8) operably linked in a non-native conformation to a human TNNT1 basal promoter having a nucleic acid sequence corresponding to SEQ ID NO: 5 or 6, is capable of directing expression of an expressible sequence which is operably linked downstream of the TNNT1 promoter in specific cell types in different regions of the brain, heart or skeletal muscle. It is within the skill of one in the art to locate and determine these relative positions based on published sequence information for this gene, for instance found in the GenBank or PubMed public databases. It is understood that these genomic coordinates and relative positions are provided for the purposes of context, and that if any discrepancies exist between published sequences and the sequence listings provided herein, then the sequence listings shall prevail.

Promoters of the present invention may be modified with respect to the native regulatory and/or native basal promoter sequence. In general, such modifications will not change the functional activity of the promoter with respect to cell-type selectivity; and to the rate of transcription in cells where the promoter is active. The modified promoter provide for a transcription rate of an expressible sequence operably linked to a modified promoter sequence that is at least about 75% the transcription rate of the promoter sequence of SEQ ID NO: 1-4, at least about 80%, at least about 90%, at least about 95%, at least about 99%, or more. Methods of assessing promoter strength and selectivity are known in the art, including, for example, expression of a reporter sequence in a cell in vivo or in vitro, and quantitating the reporter activity.

Modifications of interest include deletion of terminal or internal regions, and substitution or insertion of residues. The spacing of conserved sequences may be the same as the native spacing, or it may be different than the native spacing. The order of the conserved sequences may be the same as the native order or the sequences may be rearranged. Sequences set forth in SEQ ID NO: 1-4 that are not conserved may be deleted or substituted, usually modifications that retain the spacing between conserved sequences is preferred. In general the spacing between the regulatory element and the basal promoter is not more than about 10 KB, generally not more than about 1 KB, usually not more than about 500 nt, and may be not more than about 100 nt, down to a direct joining of the two sequences.

In one embodiment of the invention, there is provided an isolated nucleic acid fragment comprising a TNNT1 mini-promoter, wherein the TNNT1 mini-promoter comprises a TNNT1 regulatory element operably linked in a non-native conformation to a TNNT1 basal promoter. The TNNT1 mini-promoter may have a nucleic acid sequence which is substantially similar in sequence and function to SEQ ID NO: 1-4. The TNNT1 basal promoter may have a nucleic acid sequence which is substantially similar in sequence and function to SEQ ID NO: 5 or 6. The TNNT1 regulatory element may have a nucleic acid sequence which is substantially similar in sequence and function to SEQ ID NO: 7-9. In other embodiments, there is provided an isolated nucleic acid fragment comprising a TNNT1 mini-promoter, wherein the TNNT1 mini-promoter comprises a TNNT1 basal promoter. The TNNT1 basal promoter may have a nucleic acid sequence which is substantially similar in sequence and function to SEQ ID NO: 5 or 6. The TNNT1 mini-promoters may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule.

It is an object of the present invention to provide means of expressing a gene, protein, RNA interference molecule or the like in a cell, tissue or organ. As such, the inventors thus provide novel expression vectors comprising TNNT1 mini-promoters which are capable of accomplishing this task. In one embodiment, there is provided an expression vector comprising a TNNT1 mini-promoter, wherein the TNNT1 mini-promoter comprises a TNNT1 regulatory element operably linked in a non-native conformation to a TNNT1 basal promoter. The TNNT1 mini-promoter may have a nucleic acid sequence which is substantially similar in sequence and function to SEQ ID NO: 1-4. The TNNT1 basal promoter may have a nucleic acid sequence which is substantially similar in sequence and function to SEQ ID NO: 5 or 6. The TNNT1 regulatory element may have a nucleic acid sequence which is substantially similar in sequence and function to SEQ ID NO: 7-9. In other embodiments, there is provided an expression vector comprising a TNNT1 mini-promoter, wherein the TNNT1 mini-promoter comprises a TNNT1 basal promoter. The TNNT1 basal promoter may have a nucleic acid sequence which is substantially similar in sequence and function to SEQ ID NO: 5 or 6. The TNNT1 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may further comprise a genomic targeting sequence. The genomic targeting sequence may be HPRT, e.g. human HPRT, mouse HPRT, etc.

The inventors have herein demonstrated that expression vectors comprising novel TNNT1 mini-promoter elements are capable of directing transcription of an expression sequence in specific cell types, for instance in neuronal cells in the brain or muscle cells in striated or cardiac muscle tissue. In one embodiment of the invention, there is thus provided a method for expressing a gene, protein, RNA interference molecule or the like in a cell, the method comprising introducing into the cell an expression vector comprising a TNNT1 mini-promoter element, wherein the TNNT1 mini-promoter element comprises a TNNT1 regulatory element operably linked in a non-native conformation to a TNNT1 basal promoter element. In another embodiment, the TNNT1 mini-promoter comprises a TNNT1 basal promoter. Cells of interest include, without limitation, cells of the peripheral or central nervous system and progenitors thereof, e.g. embryonic stem cells, neural stem cells, neurons, glial cells, astrocytes, microgial cells, etc. or cells of striated, cardiac or smooth muscle throughout the body and progenitors thereof, e.g. satellite cells, cardiomyocytes, myocytes, myoblasts, etc.; The TNNT1 mini-promoter may have a nucleic acid sequence which is substantially similar in sequence and function to SEQ ID NO: 1-4. The TNNT1 regulatory element may have a nucleic acid sequence which is substantially similar in sequence and function to SEQ ID NO: 7-9. The TNNT1 basal promoter may have a nucleic acid sequence which is substantially similar in sequence and function to SEQ ID NO: 5 or 6. The TNNT1 mini-promoter may further be operably linked to an expressible sequence, e.g. reporter genes, genes encoding a polypeptide of interest, regulatory RNA sequences such as miRNA, siRNA, antisense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may thus further comprise a genomic targeting sequence. The genomic targeting sequence may be HPRT.

In one embodiment of the invention, there is provided a method for identifying or labeling a cell, the method comprising introducing into the cell an expression vector comprising a TNNT1 mini-promoter element, wherein the TNNT1 mini-promoter element comprises a TNNT1 regulatory element operably linked in a non-native conformation to a TNNT1 basal promoter element, and wherein the expressible sequence comprises a reporter gene. In other embodiments, the TNNT1 mini-promoter comprises a TNNT1 basal promoter. The TNNT1 mini-promoter element may have a nucleic acid sequence substantially similar in sequence and function to SEQ ID NO: 1-4. The TNNT1 regulatory element may have a nucleic acid sequence substantially similar in sequence and function to SEQ ID NO: 7-9. The TNNT1 basal promoter element may have a nucleic acid sequence substantially similar in sequence and function to SEQ ID NO: 5 or 6. The inventors have demonstrated that expression vectors comprising certain human TNNT1 promoter elements are capable of expression in specific regions of the brain and in muscle cells. In some embodiments, the cell is a peripheral or central nervous system cell or progenitors thereof, including, without limitation, embryonic stem cells, neural stem cells, glial cell, neuronal cells, astrocytes, and the like, or cells of striated, cardiac or smooth muscle throughout the body and progenitors thereof, including, without limitation, satellite cells, cardiomyocytes, myocytes, myoblasts, and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In further embodiments of the invention, there is provided a method for monitoring or tracking the development or maturation of a cell, the method comprising: 1) introducing into the cell a expression vector comprising a TNNT1 mini-promoter element operably linked to an expressible sequence, wherein the TNNT1 mini-promoter element comprises a TNNT1 regulatory element operably linked in a non-native conformation to a TNNT1 basal promoter element, and wherein the expressible sequence comprises a reporter gene; and 2) detecting the expression of the reporter gene in the cell of in progeny of the cell as a means of determining the lineage, identity or developmental state of the cell or cell progeny. In other embodiments, the TNNT1 mini-promoter comprises a TNNT1 basal promoter. The TNNT1 mini-promoter element may have a nucleic acid sequence substantially similar in sequence and function to SEQ ID NO: 1-4. The TNNT1 regulatory element may have a nucleic acid sequence substantially similar in sequence and function to SEQ ID NO: 7-9. The TNNT1 basal promoter element may have a nucleic acid sequence substantially similar in sequence and function to SEQ ID NO: 5 or 6. In such a fashion, one may be able to follow the development of a parent cell as it differentiates into more mature cells. As an example, one could introduce an expression vector comprising the aforementioned TNNT1 mini-promoter elements into a pluripotent stem cell, monitor the expression of the reporter gene that is being expressed by the TNNT1 promoter elements during the maturation and differentiation of the stem cell and thus determine the state of maturation, for instance in the differentiation of the pluripotent stem cell into a specific brain cell type. The inventors have demonstrated that the TNNT1 mini-promoter elements described herein direct transcriptional expression in certain brain cell types, and so detection of reporter gene expression in a cell would thus be indicative of the cellular identity of the cell as being a certain type of brain cell. The inventors have also demonstrated that the TNNT1 mini-promoter elements described herein direct transcriptional expression in certain muscle cell types, and so detection of reporter gene expression in a cell would thus be indicative of the cellular identity of the cell as being a certain type of muscle cell.

The inventors have herein demonstrated that certain TNNT1 mini-promoter elements of the present invention are capable of driving expression in the thalamus region of the brain. This surprising expression pattern provides additional methods of use for these mini-promoter elements. For instance, it may be desirable to utilize the TNNT1 mini-promoters of the present invention in a gene therapy or cell therapy application wherein the TNNT1 mini-promoters are utilized to drive expression of a therapeutic or beneficial compound, such as a protein, in neuronal cells. In such a way, the therapeutic or beneficial compound may be useful for a disease or condition that involves such neuronal cells, involves expression of a therapeutic molecule in the thalamus, or which may be improved by expression of the therapeutic or beneficial compound in those cells or other supporting cells in the central nervous system. In certain embodiments of the invention, there is thus provided a method of treatment of a subject having a disease involving the serotonergic system the method comprising administering to the subject a therapeutically effective dose of a composition comprising a TNNT1 mini-promoter element, wherein the TNNT1 mini-promoter element comprises a TNNT1 regulatory element operably linked in a non-native conformation to a TNNT1 basal promoter element. In another embodiment, the TNNT1 mini-promoter comprises a TNNT1 basal promoter. The TNNT1 mini-promoter element may have a nucleic acid sequence substantially similar in sequence and function to SEQ ID NO: 1-4. The TNNT1 regulatory element may have a nucleic acid sequence substantially similar in sequence and function to SEQ ID NO: 7-9. The TNNT1 basal promoter element may have a nucleic acid sequence substantially similar in sequence and function to SEQ ID NO: 5 or 6. The disease or condition may be chosen from: hypothalamus or thalamus related brain disorders, nemaline myopathies, muscular dystrophies, heart failure or defects, or other muscle-related disorders.

The inventors herein further describe the present invention by way of the following non-limiting examples:

WORKING EXAMPLES

General Methods

Expression Vector

The nucleic acid fragment corresponding to SEQ ID NO: 1-4 was inserted into the multiple cloning site of pEMS1313 (driving the lacZ reporter) to produce the expression vectors that were used in the experiments. The table below (Table 1) shows the sequence identifier and construct names for each mini-promoter. FIG. 1 illustrates the design of the pEMS1100 construct containing the Ple232 mini-promoter.

| Construct name | Mini-Promoter Name | Corresponding nucleic acid fragmen inserted into pEMS1313 vector | Size in nucleotide base pairs |
|---|---|---|---|
| pEMS2026 | Ple301 | SEQ ID NO: 2 | 1209 |
| pEMS1100 | Ple232 | SEQ ID NO: 1 | 1209 |
| TNNT1-A | Ple231 | SEQ ID NO: 3 | 1250 |
| TNNT1-C | Ple233 | SEQ ID NO: 4 | 1208 |

Blastocysts were obtained from natural mating of B6-Hprtb-m3 homozygous females to 129-ROSA26 heterozygous males at 3.5 dpc. Blastocysts were flushed from uterine horns as per (Hogan, Beddington et al. 1994), cultured in EmbryoMax® KSOM with ½ Amino Acids, Glucose and Phenol Red (Cat # MR-121, Millipore/Chermicon, Temecula, Calif.) for 3-5 h, and then transferred onto mitomycin C (mitC; Cat#M4287, Sigma, Oakville, ON) mitotically inactivated B6-Hprtb-m3, B6129F1, or 129 mouse embryonic feeders (MEFs) derived from 13.5-day post-coital embryos (Ponchio, Duma et al. 2000) in 96-well plates containing KSR-ESC (Knockout™ D-MEM, Cat#10829-018, Invitrogen, Burlington, ON) with 2 mM L-glutamine (Cat#25030-081, Invitrogen, Burlington, ON), 0.1 mM MEM nonessential amino acid solution (Cat#11140-050, Invitrogen, Burlington, ON) and 16% Knockout™ Serum Replacement (Cat#10828-028, Invitrogen, Burlington, ON)) media (MEF media was replaced 3-5 hour prior to transfer). Blastocysts were cultured as per (Cheng, Dutra et al. 2004) with the following modifications: Cells were cultured for 7-9 days in KSR-ESC with minimal disturbance (checked on day 2 to determine if the blastocysts had 'hatched' out of the zona pellucida) and no media changes. Blastocysts which hatched and had a well-developed ICM (inner cell mass) were treated with 20 µl 0.25% trypsin-EDTA (Invitrogen, Burlington, ON) for 5 min at 37° C., triturated with a 200 µl Pipetman, inactivated with 30 µl 0.5 mg/ml soybean trypsin inhibitor (Invitrogen, Burlington, ON), and brought up to 200 µl with KSR-ESC, then transferred individually to a 24-well MEF plate containing 1800 µl KSR-ESC, for a total volume of 2 ml. Beginning 4 days later, KSR-ESC media was replaced with FBS-ESC media (DMEM (Cat #11960-069, Invitrogen, Burlington, ON) with 2 mM L-glutamine (Invitrogen, Burlington, ON), 0.1 mM MEM nonessential amino acid solution (Invitrogen, Burlington, ON), 16% ES Cell Qualified fetal bovine serum (FBS, Invitrogen, Burlington, ON), 1000 U ESGRO-LIF (Millipore, ESG1107) and 0.01% β-mercaptoethanol (Sigma, Oakville, ON)) in 25%, 50%, 75% proportions (respectively) to adapt the cells to FBS-containing media. On day 7 the cells were trypsinized to one well of a 24 well plate containing 1 ml of 100% FBS-ESC media, with daily media replacement. Once confluent, wells containing ESC colonies were expanded 3×24 wells (with MEFs), then passaged to 3×24 (with MEFs) and 3×12 well (plastic—no MEFs) for DNA analysis. Once confluent, the 3×24 wells were combined, aliquoted (3 vials), and frozen in ESC-freeze media (50% FBS, 40% FBS-ESC media, 10% DMSO (Sigma, Oakville, ON), and the 3×12 well treated with lysis buffer (Fisher Scientific, Ottawa, ON), mixed and aliquoted. Cultures were genotyped for X & Y chromosomes (Clapcote and Roder 2005), Gt(ROSA)26Sortm1Sor and WT alleles and Hprtb-m3 and WT alleles. B6129F1-Gt(ROSA)26Sortm1Sor/+, Hprtb-m3/Y (mEMS1204 series) and B6129F1-Gt(ROSA)26Sortm1Sor+/+, Hprtb-m3/Y (mEMS1202 series) cell lines were identified.

Knock-in at the Hprt Locus

The expression vector plasmid DNA was purified with Qiagen Maxi Kit (Qiagen, Mississauga, ON), resuspended in 10:1 Tris-EDTA (TE, pH7.0) buffer, and linearized with I-SceI (New England Biolabs, Pickering, ON). Linearized plasmid DNA was resuspended in 85 µl of TE (10:0.1) to a final concentration of 187.5 ng/µl. Ple232 was targeted in our in-house derived mEMS1202 cell line. ESCs were grown to confluence on 4-6 T75 flasks of mitC treated Hprtb-m3 mouse embryonic feeders (MEFs) in FBS-ESC media. ESCs (1.7-2.5×10⁷) in 720 µl 1×PBS were added to the linearized DNA and electroporated in a 4 mm electroporation cuvette (Bio-Rad Genepulser, Mississauga, ON), at 240 V, 50 µF, 6-10 msec pulse, immediately resuspended in a total volume of 5 ml of FBS-ESC media and plated onto 5×100 mm dishes of mitC B6129F1 MEFs in a total volume of 12 ml per 100 mm dish. 24-36 h post-electroporation, correctly targeted homologous recombinants were selected for using HAT media (FBS-ESC media containing 1×HAT ((0.1 mM sodium hypoxanthine, 0.4 mM aminopterin, 0.16 mM thymidine), Cat#21060-017, Invitrogen, Burlington, ON). HAT media was changed every day for the first 3 days, and then every 3rd day thereafter, for up to 10 days. Individual colonies were counted and, typically, no more than 2 isolated colonies were picked per 100 mm dish to optimize for independent homologous recombination events. These colonies were expanded under standard protocols for verification of the desired recombination event.

Derivation of Knock-in Mice

Chimeric mice from targeted ESCs were generated by microinjection (Hogan, Beddington et al. 1994) into E3.5 blastocysts followed by implantation into the uterine horns of 2.5 day pseudopregnant ICR females. Chimeras were identified and coat color chimerism determined as outlined below.

Male chimeras derived from the E14TG2a cell lines were mated with B6 or B6-Alb females, and germline transmission was identified in the former case by the transmission of the dominant Aw (white bellied agouti) allele, making the progeny appear brown with a cream belly, or in the latter case by the combination of Aw and Tyrc-ch (chinchilla), making the progeny appear golden. Non-germline progeny from the cross to B6 were homozygous for the recessive a (nonagouti) allele and appeared black, whereas non-germline progeny from the cross to B6-Alb were homozygous for the recessive Tyrc-2J (albino 2 Jackson) allele and appeared white.

Male chimeras derived from the cell lines were mated with B6-Alb females, and germline transmission identified by the presence of the dominant Tyr+ (tyrosinase; wild type) and the Aw (white bellied agouti) or a (nonagouti) alleles making the progeny appear brown with a cream belly or black, respectively. Non-germline progeny were homozygous for the recessive Tyrc-2J (albino 2 Jackson) allele and appeared white. All germline female offspring carry the knock-in X Chromosome and were mated with B6 males. N2 offspring were analyzed for the presence of the KI allele by PCR.

Reporter Gene Detection

Adult male hemizygous MiniPromoter and age matched control mice were perfused with 4% paraformaldehyde (PFA) as previously described (Young, Berry et al. 2002). Whole brains were dissected out and post-perfusion immersion fixed with PFA for 2 hours at 4° C. The brains were sectioned using a coronal or sagittal brain mold (Electron Microscopy Sciences) at 1 mm and sections were placed in 12-well tissue culture plates. In brief, brain sections were rinsed with phosphate buffered saline (PBS), then incubated with X-Gal (Boeringer Mannheim, Indianapolis, Ind.) at 37° C., usually overnight. After staining the tissue was rinsed with PBS and moved into PBS containing 0.02% azide for storage. Bright field images were taken on a Leica MZ125 dissecting microscope and photographed using an Olympus Coolsnap cf color camera with the ImagePro software package.

Virus Production

The Ple301 was generated by direct synthesis by DNA2.0 (Menlo Park, Calif., USA) (SEQ ID NO: 2). Promoter elements were cloned into the pEMS1980 backbone, containing the iCre reporter, using AvrII and AscI restriction enzymes. One µg of pEMS2026 plasmid containing either the Ple301 MiniPromoter was prepared by miniprep and sent to the Vector Core at the University of Pennsylvania (Philadelphia, Pa., USA) to be made into AAV9 serotype virus.

Virus Injection

B6-Gt(ROSA26)$^{tm1Sor}$ females were crossed to 129-Gt (ROSA26)$^{tm1Sor}$ to yield hybrid F1 homozygous pups for injecting virus. Plug checks were performed on the females such that the day of birth could be accurately estimated. P0 pups were used for virus injections. If the female gave birth in the morning, virus was injected in the afternoon. If she gave birth in the afternoon, virus was injected the next morning. A standard injection into the superficial temporal vein of a newborn pup was performed using $1 \times 10^{13}$ GC/mL (genome copies per milliliter) virus in a total volume of 50 µL (in PBS) with a 30 gauge needle and a 1 cc syringe. After injections, pups were tattooed for identification and returned to their cage.

Harvesting of Animals

Virus-injected mice were harvested at P21 or P56 (postnatal day 21 or 56). Animals were given a lethal dose of avertin injected intraperitoneally. Thereafter perfusion with 1×PBS for 2 minutes and 4% PFA/PBS for 8 minutes was performed. Tissues were harvested and post-fixed for 1 hour at 4° C. The tissues were then stored in 0.02% Azide/PBS at 4° C.

Histology

Tissues were cryoprotected in 30% sucrose/PBS overnight at 4° C. After embedment in OCT the following day, 20 µm sections were directly mounted onto slides. For X-gal staining, tissues were rinsed in PBS and Triton-X/PBS and stained in 0.1% X-gal solution overnight at 30-35° C. After staining sections were rinsed and counterstained with neutral red, dehydrated and mounted with coverslips. For co-labeling of X-gal with markers using immunohistochemistry, standard IHC procedure was followed and the X-gal stain was performed either prior to primary antibody incubation or between primary and secondary antibodies, depending on the strength of the X-gal stain. X-gal stains blue any cells that have recombined the Gt(ROSA26)$^{tm1Sor}$ locus due to iCre recombinase activity and thus expressing the β-galactosidase protein.

Example 1

Selection of TNNT1 Mini-Promoter Elements

TNNT1 basal promoter regions were tested with three selected regulatory regions of the human TNNT1 promoter region. The basal promoters included the basal promoter of 340 bp (SEQ ID NO: 5 or 6). Experiments also included the basal promoter (SEQ ID NO: 5) fused to regulatory region 2 (SEQ ID NO: 8) called Ple232 (SEQ ID NO: 1) and the basal promoter (SEQ ID NO:6) fused to regulatory region 2 (SEQ ID NO: 8) called Ple301 (SEQ ID NO: 2). FIG. 1 shows the organization of the Ple232 construct.

Example 2

Expression of Reporter in Brain by the Ple232 Mini-Promoter Construct

Figure 2A:
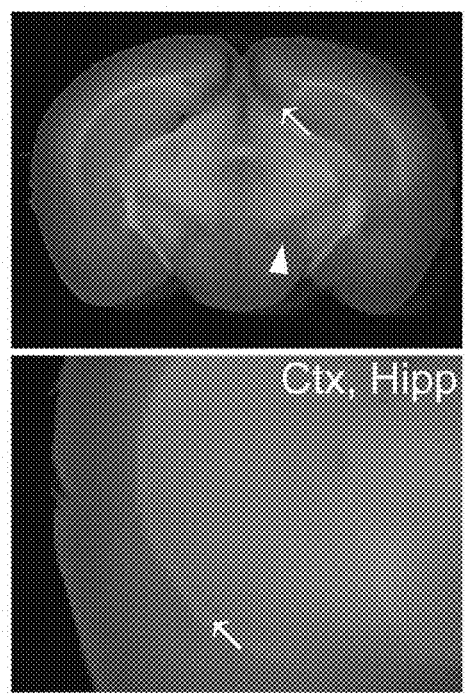
FIG. 2A-2B—The Ple232 construct expresses in embryos and in the adult mouse brain. The Ple232 promoter driving beta-galactosidase (lacZ) expression was constructed and knocked-in as a single-copy at the mouse Hprt locus for reproducible expression. Adult mice were harvested via perfusion and stained overnight for lacZ activity (blue), indicative of promoter activity.
Figure 2B:
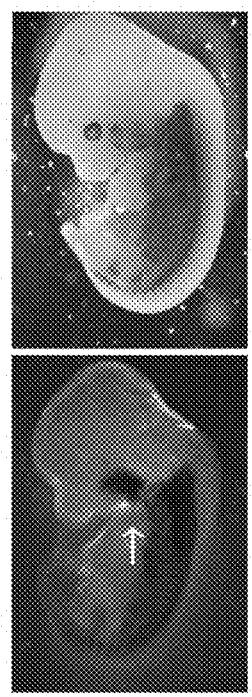

The Ple232 construct subsequently tested as a single-copy site-specific knock-in at the mouse Hprt locus as previously published (Yang et al. 2009; Portales-Casamar et al. 2010; de Leeuw et al. 2014). Mice were harvested by cardiac perfusion, sectioned, and stained with the X-gal substrate, which leaves a blue product after enzymatic cleavage by beta-galactosidase (encoded by the lacZ reporter). In the brain, Ple232-driven lacZ expression was detected in the retrosplenial and orbital cortical layers, including the anterior cingulate (FIG. 2A, top). There was also some staining in the hippocampus. The zona incerta and other small thalamic and hypothalamic regions were positive for lacZ (FIG. 2A, bottom). Some scattered cells were observed in the periaqueductal grey and in the superior colliculi. When analyzed at E12.5 in whole mount embryos, we observed staining associated with the developing musculature of the embryo (FIG. 2B), consistent with a role for this gene in slow skeletal muscle (Kee and Hardeman 2008; Johnston et al. 2000). There were a few striations in the developing heart (FIG. 2B, bottom panel, arrow), consistent with cardiac expression literature for Tnnt1 (Manuylov and Tevosian 2009). The adult mouse heart was also positive (not shown).

Example 3

Expression of Reporter in the Skeletal Muscle and Heart by the Ple301 Mini-Promoter Construct The Ple301 construct was designed based on the TNNT1 gene, and includes one nucleotide change to each of two elements, DCE1 and DCE2, relative to the Ple232 construct. DCE elements are recognized by TAF-1 (Transcription initiation factor TFIID subunit 1), which may be necessarily to increase basal levels of transcription. The Ple301 construct subsequently tested in ssAAV9 (recombinant single-stranded adeno-associated virus) driving the icre reporter (Cre recombinase), resulting in vEMS48.

Mice were injected intravenously with virus at post-natal day 0 (P0) (method of (Foust et al. 2009)), and expression analyzed at P21 and P56 via recombination of the reporter locus Gt(ROSA26)Sor$^{tmSor1}$ (Soriano 1999). Once recombined, this locus expresses the β-galactosidase (lacZ gene) enzyme. Mice were harvested by cardiac perfusion, sectioned, and stained with the X-gal substrate, which leaves a blue product after enzymatic cleavage by beta-galactosidase.

As shown in FIG. 3, there was clear staining observed in both the skeletal muscle (quadriceps were harvested and are shown in FIG. 3A), as well as in the heart (FIG. 3B).

SEQUENCE LISTINGS

Ple232 (TNNT1-B)

SEQ ID NO: 1

```
gaaaacttagagtgccattatctggggtatcatgaactgggcctcc gagtttgggtatcaagattttgggggtctcatattcttgaggtttc agattttaggaggtctcaagacctgggggtggtcttaggatgtccc ggcccatatctggactatcaagaactgggatttcagaatccagagc tgtgaggacttgctggcctcagaaacacgggcatcataaatcgggg tctcagaatctgtgggtattgggatttggggctaggcaccctgtgg cctagggtgtctcaaagactttgaggtctaagaatgtaggggtcag ggtgaggtctacggacagaaggtgccctttatgccoctgccccta cgtgatgtatgggaaggtgaaaggggagacaggtggggaggaaacc agccagtggggtgggggcgagtgggagagggatgcgggtgactaat tctcccagaagccccccttcctcaaatcccttcttaggaaatgtcc tcggtttcaccatctatgacatccccccaaaatagctcctggggggt
```

| SEQUENCE LISTINGS |
|---|
| ggggcagctattgtcttcaggccactgtcccttctcaaatgcctct |
| tcctaatcccaactggatcaggttcccatggacttgtcataagaca |
| aaagaggacagctgtgctgaggggcagggtctgcagcctcctggc |
| tgtgccaggaccacacctaccaaggtctgtcctcatgcatgcttta |
| ggacagccggccccctccctcagacccaagagtccagacctgagcc |
| ctcctccctcagacgcaggagtacaggccccagcccgctcctccc |
| tcagactcaggagtctagactcccagcctctcccctccaaggacct |
| actgtgtgccgggcatgggacgtcaaagcacagggagctataagg |
| gaggtagttggagcaccacgggagcctggggtgtgggtgggagca |
| ggggcggggctcctgggccatgcagatggggttggcatgggttgg |
| ggaggggcccacggaggcttctggactctgagtgtggagccagggg |
| cagcagggctgtctctgaactcccaggcttgtgtttgagcaagga |
| attctctcccctccctctccctcggggcgggcccgagcctccag |
| ctataaactccccggagcttcagtgccctcagcaaggctcagcctc |
| aagattcacagca |

>Ple301_TNNT1_1209bp
SEQ ID NO: 2

| |
|---|
| GAAAACTTAGAGTGCCATTATCTGGGGTATCATGAACTGGGCCTCC |
| GAGTTTGGGTATCAAGATTTTGGGGGTCTCATATTCTTGAGGTTTC |
| AGATTTTAGGAGGTCTCAAGACCTGGGGGTGGTCTTAGGATGTCCC |
| GGCCCATATCTGGACTATCAAGAACTGGGATTTCAGAATCCAGAGC |
| TGTGAGGACTTGCTGGCCTCAGAAACACGGGCATCATAAATCGGGG |
| TCTCAGAATCGTGGGTATTGGGATTTGGGGCTAGGCACCCTGTGG |
| CCTAGGGTGTCTCAAAGACTTTGAGGTCTAAGAATGTAGGGGTCAG |
| GGTGAGGTCTACGGACAGAAGGTGCCCTTTATGCCCCTGCCCCCTA |
| CGTGATGTATGGGAAGGTGAAAGGGGAGACAGGTGGGGAGGAAACC |
| AGCCAGTGGGGTGGGGCGAGTGGGAGAGGGGATGCGGGTGACTAAT |
| TCTCCCAGAAGCCCCCCTTCCTCAAATCCCTTCTTAGGAAATGTCC |
| TCGGTTTCACCATCTATGACATCCCCCCAAAATAGCTCCTGGGGGT |
| GGGGCAGCTATTGTCTTCAGGCCACTGTCCCTTCTCAAATGCCTCT |
| TCCTAATCCCAACTGGATCAGGTTCCCATGGACTTGTCATAAGACA |
| AAAGAGGACAGCTGTGCTGAGGGGGCAGGGTCTGCAGCCTCCTGGC |
| TGTGCCAGGACCACACCTACCAAGGTCTGTCCTCATGCATGCTTTA |
| GGACAGCCGGCCCCCTCCCTCAGACCCAAGAGTCCAGACCTGAGCC |
| CTCCTCCCTCAGACGCAGGAGTACAGGCCCCAGCCCGCTCCTCCC |
| TCAGACTCAGGAGTCTAGACTCCCAGCCTCTCCCCTCCAAGGACCT |
| ACTGTGTGCCGGGCATGGGACGTCAAAGCACAGGGAGCTATAAGG |
| GAGGTAGTTGGAGCACCACGGGAGCCTGGGGTGTGGGTGGGAGCA |
| GGGGCGGGGCTCCTGGGCCATGCAGATGGGGTTGGCATGGGGTTGG |
| GGAGGGGCCCACGGAGGCTTCTGGACTCTGAGTGTGGAGCCAGGGG |

| SEQUENCE LISTINGS |
|---|
| CAGCAGGGCTGTCTCTGAACTCCCAGGCTTGTGTTTGAGCAAAGGA |
| ATTCTCTCCCCTCCCTCTCCCTCGGGGCGGGCCCGAGCCTCCAG |
| CTATAAACTTCCCGGAGCTTCTGTGCCCTCAGCAAGGCTCAGCCTC |
| AAGATTCACAGCA |

>Ple231_final
SEQ ID NO: 3

| |
|---|
| aaataccacaagatgcatagaaggaagtgcaaagaaaggagaaaag |
| agagacagagatatactcacagcaaggtgcagagacatggagaccc |
| tataagagatggaaatggagagccacagagggggaactgcgggcac |
| taagagagacatggagagaactagaaagatagagacgtgaacacag |
| acacagagacccagagccaaaaagagacagaaatgggtcataggt |
| ggacagaaatgcacagagagactgtgagcccccacagacacaaacg |
| ctgagaggggcagacatgcagagacacccacagaaatgcagagaca |
| aaaccacccggagacacatgccgagaaacacactgaggggctcaga |
| aagcgacagatgcagagagagcccaagacagacccagcaaggggcc |
| ccgagaaatgcacagaaacaaagaccgagaccaccagagacaga |
| ggtacggagaggcgggagggtgaggaagcctgctctccagggctg |
| gcttgaacctagaactcaaggtcatggcttggctgggaagcgggag |
| ggggataccaaaaaagatcagcgttagatggaggtggggagggagg |
| gtaggtttcaccctaattgacaccccaccctcccctccccctccc |
| cacacctgcttccggctttagtgcctgttgtgtcaccaggatggaat |
| cctggcggcagacaaaggggtgggggtgggaggaggagacaaaaag |
| atggacagagacagaggaggagactaagaagtagagacagacacac |
| agagacacacagatggagagccacagagacaacagaaatgggggtc |
| cagaaagagacctagatagaaagagggaacagagagaagaaaacag |
| gaaacattccttatagcccatgtgtcattagtaggtcctccaagga |
| cctactgtgtgccgggcatgggacgtcaaagcacagggagctata |
| agggaggtagttggagcaccacgggagcctggggtgtgggtggga |
| gcaggggcggggctcctgggccatgcagatggggttggcatgggt |
| tggggaggggcccacggaggcttctggactctgagtgtggagccag |
| gggcagcagggctgtctctgaactcccaggcttgtgtttgagcaaa |
| ggaattctctcccctccctctccctcggggcgggcccgagcctc |
| cagctataaactccccggagcttcagtgccctcagcaaggctcagc |
| ctcaagattcacagca |

>Ple233_final
SEQ ID NO: 4

| |
|---|
| gtaaccgcggctgcttcgcttcccgagaccgatgtcggggccggg |
| ggggaccccgatatcctcgggcccaacctccaagaccaccctcc |
| cctccctccgccccataacccgccccaggcccggtcctttaagc |
| ccctgagagctcctgcgccctctcggggccgggaagggaaatggcc |
| ccgcagtggctttaacccttccccttccttcttaaagggaccgaca | cccaagccttcttccccagtctggaggaatctttacagaagggttg
gatgtttgcggagaagcaccaccccatccccccttatcttcgcctc
caaccttgtctgttattttctcccccatatacattcaaaggttggg
gcttggaatttaggattgcagaggaggcgagcgctgggagtcaggg
tctccaaggtcgggccgggggcggggggcggtggggcggtgggca
gggggcgagctggggagagagcgctggggtcactgaatgaagacag
aggttgggaccccctgcactgctgggtcctaatggaggagagcagg
agctctgggcatataaatagagaaaggtctgggggtttgcactcct
gggtgtgcagacagtgggggtgggggtccccacaccagttctgaa
tgtatatctgatgcgtgtgaccctcttcctcctttacagccaccct
gactttccttccctcttttcttctccccatccccctcctccagaa
ctggactccagagtccttcctgggtcctggggccgaggcttgg
ggggtccctccccaggtgtgtcaggcctagcccctctcctctaaa
ctcttgctaattatctcttttatccccaccaccaacagcctcca
aggacctactgtgtgccgggcatggggacgtcaaagcacagggagc
tataagggaggtagttggagcaccacgggagcctggggtgtgggt
gggagcaggggcgggctcctgggccatgcagatggggttggcatg
gggttggggaggggcccacggaggcttctggactctgagtgtggag
ccaggggcagcagggctgtctctgaactcccaggcttgtgtttgag
caaaggaattctctccccctccctctccctcggggcgggcccgag
cctccagctataaactccccggagcttcagtgccctcagcaaggct
cagcctcaagattcacagca >TNNT1-Prom_
SEQ ID NO: 5
Cctccaaggacctactgtgtgccgggcatggggacgtcaaagcaca
gggagctataagggaggtagttggagcaccacgggagcctggggtg
tggggtgggagcaggggcgggctcctgggccatgcagatggggtt
ggcatgggttggggaggggcccacggaggcttctggactctgagt
gtggagccaggggcagcagggctgtctctgaactcccaggcttgtg
tttgagcaaaggaattctctccccctccctctccctcggggcggg
cccgagcctccagctataaactccccggagcttcagtgccctcagc
aaggctcagcctcaagattcacagca TNNT1-Prom
SEQ ID NO: 6
Cctccaaggacctactgtgtgccgggcatggggacgtcaaagcaca
gggagctataagggaggtagttggagcaccacgggagcctggggtg
tggggtgggagcaggggcgggctcctgggccatgcagatggggtt
ggcatgggttggggaggggcccacggaggcttctggactctgagt
gtggagccaggggcagcagggctgtctctgaactcccaggcttgtg
tttgagcaaaggaattctctccccctccctctccctcggggcggg
cccgagcctccagctataaactcccggagcttctgtgccctcagc
aaggctcagcctcaagattcacagca >Reg1
SEQ ID NO: 7
aaataccacaagatgcatagaaggaagtgcaaagaaaggagaaaag
agagacagagatatactcacagcaaggtgcagagacatggagaccc
tataagagatggaaatggagagccacagagggggaactgcgggcac
taagagagacatggagagaactagaaagatagagacgtgaacacag
acacagagacccagagccaaaaagagacagaaatgggggtcataggt
ggacagaaatgcacagagagactgtgagcccccacagacacaaacg
ctgagaggggcagacatgcagagacacccacagaaatgcagagaca
aaaccaccggagacacatgccgagaaacacactgaggggctcaga
aagcgacagatgcagagagagcccaagacagacccagcaagggcc
ccgagaaatgcacagaaacacaaagaccgagaccaccagagacaga
ggtacggagaggcgggagggtgaggaagcctgctctccagggctg
gcttgaacctagaactcaaggtcatggcttggctgggaagcgggag
ggggataccaaaaaagatcagcgttagatggaggtggggagggagg
gtaggtttcaccctaattgacaccccaccctccccctcccccctccc
cacacctgcttccggctttagtgcctgttgtcaccaggatggaat
cctggcggcagacaaaggggtgggggtgggaggaggagacaaaaag
atggacagagacagaggaggagactaagaagtagagacagacacac
agagacacacagatggagagccacagagacaacagaaatgggggtc
cagaaagagacctagatagaaagagggaacagagagaagaaaacag
gaaacattccttatagcccatgtgtcattagtaggt >TNNT1-2
SEQ ID NO: 8
gaaaacttagagtgccattatctgggtatcatgaactgggcctcc
gagtttgggtatcaagatttgggggtctcatattcttgaggtttc
agattttaggaggtctcaagacctgggggtggtcttaggatgtccc
ggcccatatctggactatcaagaactgggatttcagaatccagagc
tgtgaggacttgctggcctcagaaacacgggcatcataaatcgggg
tctcagaatctgtgggtattgggatttgggctaggcaccctgtgg
cctagggtgtctcaaagactttgaggtctaagaatgtagggtcag
ggtgaggtctacggacagaaggtgccctttatgcccctgccccta
cgtgatgtatgggaaggtgaaaggggagacaggtggggaggaaacc
agccagtggggtgggcgagtgggagagggatgcgggtgactaat
tctcccagaagcccccttcctcaaatcccttcttaggaaatgtcc
tcggtttcaccatctatgacatcccccaaaatagctcctgggggt
gggcagctattgtcttcaggccactgtcccttctcaaatgcctct
tcctaatcccaactggatcaggttcccatggacttgtcataagaca
aaagaggacagctgtgctgaggggcagggtctgcagcctcctggc tgtgccaggaccacacctaccaaggtctgtcctcatgcatgcttta ggacagccggccccctccctcagacccaagagtccagacctgagcc ctcctccctcagacgcaggagtacaggccccagcccgctcctccc tcagactcaggagtctagactcccagcctctcc

>TNNT1-3

SEQ ID NO: 9 gtaaccgcggctgcttcgcttcccgagaccgatgtcggggggccgg ggggaccccgatatcctcgggcccaacctccaagaccaccccttc cctccctccgcccccataacccgcccccaggcccggtcctttaagc ccctgagagctcctgcgccctctcggggccgggaagggaaatggcc ccgcagtggctttaaccctttccttccttcttaaagggaccgaca cccaagccttcttccccagtctggaggaatctttacagaagggttg gatgtttgcggagaagcaccaccccatcccccttatcttcgcctc caaccttgtctgttattttctcccccatatacattcaaaggttggg gcttggaatttaggattgcagaggaggcgagcgctgggagtcaggg tctccaaggtcgggccggggcggggggcggtggggcggtgggca ggggggcgagctggggagagagcgctggggtcactgaatgaagacag aggttgggacccctgcactgctgggtcctaatggaggagagcagg agctctgggcatataaatagagaaaggtctgggggtttgcactcct gggtgtgcagacagtgggggtggggggtccccacaccagttctgaa tgtatatctgatgcgtgtgaccctcttcctccttacagccaccct gactttccttccctcttttcttctcccatccccctcctccagaa ctggactccagagtccttccctggggtcctgggggcgaggcttgg ggggtccctcccagggtgtgtcaggcctagcccctctcctctaaa ctcttgctaattatctctttttatccccaccaccaacag

What is claimed is:

1. An isolated polynucleotide comprising a TNNT1 mini-promoter wherein the TNNT1 mini-promoter comprises a TNNT1 regulatory element with at least 95% sequence identity to SEQ ID NO: 8 operably joined to a TNNT1 basal promoter with a sequence identical to SEQ ID NO: 6 through a non-native spacing between the regulatory element and the basal promoter of less than 500 nt.

2. The polynucleotide of claim 1 comprising a TNNT1 mini-promoter with at least 99% sequence identity to SEQ ID NO: 2.

3. The polynucleotide of claim 1 comprising a TNNT1 mini-promoter with a sequence identical to SEQ ID NO:2.

4. The isolated polynucleotide of claim 1, operably linked to an expressible sequence.

5. A vector comprising the isolated polynucleotide of claim 1.

6. An isolated cell comprising the vector of claim 5.

7. The cell of claim 6, wherein the vector is stably integrated into the genome of the cell.

8. The cell of claim 6, wherein the cell is a stem cell, brain cell, cardiac cell or muscle cell.

* * * * *